United States Patent
Terwey et al.

(10) Patent No.: US 9,603,589 B2
(45) Date of Patent: Mar. 28, 2017

(54) DELIVERY TIP FOR EXTRAVASCULAR BIOADHESIVE CATHETER AND METHODS

(71) Applicant: St. Jude Medical Puerto Rico LLC, Caguas, PR (US)

(72) Inventors: Russell D. Terwey, St. Michael, MN (US); Zachary J. Tegels, Minneapolis, MN (US); Edward E. Parsonage, St. Paul, MN (US); Robert M. Vidlund, Forest Lake, MN (US); Martha Escobar, Jordan, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 193 days.

(21) Appl. No.: 13/778,624

(22) Filed: Feb. 27, 2013

(65) Prior Publication Data

US 2014/0135824 A1    May 15, 2014

Related U.S. Application Data

(60) Provisional application No. 61/726,220, filed on Nov. 14, 2012.

(51) Int. Cl.
*A61B 17/08* (2006.01)
*A61D 1/00* (2006.01)
(Continued)

(52) U.S. Cl.
CPC .. *A61B 17/0057* (2013.01); *A61B 2017/0065* (2013.01); *A61B 2017/22067* (2013.01)

(58) Field of Classification Search
CPC ................ A61B 17/0057; A61B 17/00; A61B 17/00491; A61B 17/12136; A61B 2017/0065; A61B 2017/00654; A61B 2017/00495; A61B 2017/00623; A61B 2017/00884; A61B 2017/00951; A61B 2017/00637; A61B 2017/00672; A61L 2400/04; A61L 2400/06; A61L 24/00; A61M 2025/0233; A61M 2025/1052;
(Continued)

(56) References Cited

U.S. PATENT DOCUMENTS 6,045,570 A    4/2000  Epstein et al.
8,333,787 B2   12/2012 Pipenhagen et al.
(Continued)

FOREIGN PATENT DOCUMENTS

EP    1 442 709 A1    8/2004
WO    03105697 A1    12/2003

OTHER PUBLICATIONS

PCT International Search Report for International Application No. PCT/US2013/027852, dated Sep. 25, 2013 (5 pp.).
(Continued)

*Primary Examiner* — Katherine M Shi
*Assistant Examiner* — Mohamed Gabr
(74) *Attorney, Agent, or Firm* — Holland & Hart (57) ABSTRACT

A vascular closure device includes an inflation balloon and a delivery tube. The delivery tube includes an inflation lumen configured to deliver inflation fluid to the inflation balloon, a sealant lumen configured to deliver a sealant to a vessel puncture, and a delivery tip in flow communication with the sealant lumen and having a plurality of outlet openings.

15 Claims, 10 Drawing Sheets

(51) Int. Cl.
*A61B 17/00* (2006.01)
*A61B 17/22* (2006.01)

(58) Field of Classification Search
CPC .......... A61M 2025/1086; A61M 25/04; A61M 16/0481; A61M 3/0279; A61M 5/19
USPC ..... 606/213, 214, 215, 216, 151, 41, 29, 42, 606/27, 28, 30, 31; 604/57, 59, 60, 96.01, 604/164.02, 164.03, 164.1, 168, 167.02, 604/168.01, 103.01, 264, 507; 424/443, 424/448
See application file for complete search history.

(56) References Cited

U.S. PATENT DOCUMENTS

| | | |
|---|---|---|
| 8,506,592 B2 | 8/2013 | Killion et al. |
| 2004/0176801 A1* | 9/2004 | Edwards et al. ............. 606/214 |
| 2009/0171282 A1* | 7/2009 | Pipenhagen et al. .... 604/103.01 |
| 2011/0166595 A1* | 7/2011 | Vidlund et al. ............... 606/213 |
| 2011/0282383 A1 | 11/2011 | Vidlund et al. |
| 2013/0006299 A1 | 1/2013 | Pipenhagen et al. |
| 2013/0190808 A1 | 7/2013 | Tegels et al. |
| 2013/0190812 A1 | 7/2013 | Vidlund |
| 2013/0190813 A1 | 7/2013 | Tegels et al. |

OTHER PUBLICATIONS

U.S. Appl. No. 13/770,586, filed Feb. 19, 2013.
U.S. Appl. No. 13/770,714, filed Feb. 19, 2013.
U.S. Appl. No. 13/772,834, filed Feb. 21, 2013.
U.S. Appl. No. 13/773,062, filed Feb. 21, 2013.
U.S. Appl. No. 13/773,206, filed Feb. 21, 2013.

* cited by examiner

DELIVERY TIP FOR EXTRAVASCULAR BIOADHESIVE CATHETER AND METHODS

CROSS-REFERENCE TO RELATED APPLICATION

This application claims the benefit of the filing date of U.S. Provisional Application No. 61/726,220, filed Nov. 14, 2012, and entitled DELIVERY TIP FOR EXTRAVASCULAR BIOADHESIVE CATHETER AND METHODS, the disclosure of which is incorporated, in its entirety, by reference.

TECHNICAL FIELD

The present disclosure relates generally to tissue puncture closure devices and methods, and more particularly, to methods and devices for delivery of bioadhesive materials to a tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one aspect of interest is the delivery of sealant material to the puncture.

SUMMARY

One aspect of the present disclosure relates to a tissue puncture closure device that includes a delivery tube having a distal end portion, a sealant lumen, and a tip portion. The distal end portion is insertable into a tissue puncture. The sealant lumen is configured to deliver a sealant to the tissue puncture. The tip portion is positioned at the distal end portion and in flow communication with the sealant lumen. The tip portion includes at least one of a different size and a different cross-sectional shaped from the sealant lumen.

The tip portion may include at least one outlet opening arranged perpendicular to the sealant lumen. The tip portion may be detachable from the delivery tube. The tip portion may be integrally formed as a single piece with the delivery tube. The tip portion may include a plurality of outlet openings. The plurality of outlet openings may be arranged facing in a distal direction. The plurality of outlet openings may be arranged facing in a direction perpendicular to the sealant lumen.

The delivery tube may include an inflation lumen and the tissue puncture closure device may include a balloon positioned at the distal end portion, wherein the balloon is connected in flow communication with the inflation lumen at a location distal of the tip portion. The delivery tube may include a plurality of sealant lumens each configured to deliver the sealant to the tissue puncture and arranged in flow communication with the tip portion. The tip portion may include at least two outlet openings.

Another aspect of the present disclosure relates to a vascular closure device that includes an inflation balloon and a delivery tube. The delivery tube includes an inflation lumen configured to deliver inflation fluid to the inflation balloon, a sealant lumen configured to deliver a sealant to a vessel puncture, and a delivery tip in flow communication with the sealant lumen and having a plurality of outlet openings.

The delivery tip may be formed integrally with the delivery tube. At least one of the outlet openings may face in a direction perpendicular to the sealant lumen. At least one of the outlet openings may have a cross-sectional size that is smaller than a cross-sectional size of the sealant lumen. The delivery tube may include a plurality of sealant lumens each connected in flow communication with the delivery tip.

Another aspect of the present disclosure relates to a method of sealing a vessel puncture. The method includes providing a vascular closure device comprising a delivery tube and a tip portion, the delivery tube including a sealant lumen and having a distal end portion, the sealant lumen being in flow communication with the tip portion. The method also includes inserting the distal end portion to the vessel puncture, delivering a volume of sealant through the sealant lumen to the tip portion, and ejecting the volume of sealant through the tip portion to deposit the volume of sealant to seal closed the vessel puncture. Ejecting the volume of fluid may include at least one of changing a direction of flow and a speed of flow as the volume of sealant moves through the tip portion.

The tip portion may include a plurality of outlet openings facing in a direction perpendicular to flow of the volume of sealant in the sealant lumen. The tip portion may include a plurality of outlet openings facing in a direction parallel to flow of the volume of sealant in the sealant lumen. The tip portion may be removable from the delivery tube. The delivery tube may include an inflation lumen, and the vascular closure device may further include a balloon mounted to the distal end portion at a location distal of the tip portion and connected in flow communication with the inflation lumen. The method may include delivering a volume of inflation fluid to the inflation balloon to inflate the inflation balloon prior to delivering the volume of sealant to the tip portion.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

The apparatuses and methods disclosed herein may be used to access percutaneous punctures made through a layer of tissue in a patient to gain access to a body cavity. Access through a percutaneous puncture allows a physician to carry out various procedures in or through the body cavity for examination, surgery, treatment and the like. While not meant to be limiting, the systems are illustrated being used to access percutaneous punctures in a tissue layer such as a blood vessel in patients for various procedures. It will be appreciated that the apparatuses and methods are applicable to other procedures requiring access to a puncture through body tissue into a cavity including, for example, laparoscopic surgery and other microscopic surgery techniques using a relatively small incision. Applications of access apparatuses and methods including those implementing principles described herein include access of a percutaneous puncture or incision in tissue separating two internal portions of a living body, such as punctures or incisions in blood vessels, ducts or lumens, gall bladders, livers, hearts, etc. Tissue puncture closure may include closure of various tissues such as a vessel puncture, and may be performed with a tissue puncture closure device such as a vascular closure device.

As used in this specification and the appended claims, the terms "engage" and "engageable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

One aspect of the present disclosure is directed to a tissue puncture closure device that provides improved mixing and delivery of a bioadhesive sealant to the tissue puncture. The tissue puncture closure device may include at least one mixing feature at a distal end of the device. The at least one mixing feature may provide additional mixing of components of the bioadhesive sealant prior to delivery to the tissue puncture. The at least one mixing feature may provide some additional mixing upon ejection of the bioadhesive sealant out of the device. The at least one mixing feature may be part of a delivery tip of the tissue puncture closure device.

The tissue puncture closure device may also include delivery tip features that provide improved control of the direction in which the bioadhesive sealant is ejected from the device. For example, a delivery tip feature of the tissue puncture closure device may direct the bioadhesive sealant in a lateral or radial direction. The delivery tip feature may provide delivery of the bioadhesive sealant in multiple directions such as, for example, in both a distal direction and a lateral or radial direction. The delivery tip feature may provide multiple openings for the bioadhesive sealant. In one example, the delivery tip feature includes multiple openings facing in a distal direction. The multiple openings may be circumferentially-spaced from each other. The plurality of openings may be arranged in flow communication with a single sealant lumen of the tissue puncture closure device. In other arrangements, each of the openings of the delivery tip feature is arranged in flow communication with a separate sealant lumen of the tissue puncture closure device.

The delivery tip feature may provide acceleration of the bioadhesive sealant just prior to ejection from the device. In at least one example, the delivery tip feature includes at least one reduced sized orifice that provides the increased acceleration. The delivery tip feature may provide a spraying function that improves dispersion and flow of the bioadhesive sealant at the tissue puncture.

The delivery tip feature may provide both improved mixing and improved control of the flow direction of the bioadhesive sealant as it is ejected from the tissue puncture closure device. The delivery tip feature may be a separate part that is assembled with a delivery tube of the tissue puncture closure device. Alternatively, the delivery tip features are at least partially integrated into a distal end portion of the delivery tube, wherein the delivery tube includes at least one sealant lumen configured to deliver the bioadhesive sealant to the distal end portion of the delivery tube.

Referring to FIGS. 1A-1D, an example vascular closure device 10 includes a manifold 12, a delivery tube 14, and a balloon location device 16. The manifold 12 includes an injection port 20 configured for attachment to a source of bioadhesive sealant. The injection port 20 is arranged in flow communication with the delivery tube 14. A latch 22 may be used to releaseably connect the vascular closure device 10 to a sheath as shown and described below with reference to FIGS. 7-10. The manifold 12 may also be constructed to permit insertion of the balloon location device 16 through the manifold 12 and into a lumen of the delivery tube 14. The balloon location device 16 may include a housing 50, an inner tube 52 having an inner tube lumen 56, an inner tube manifold 54, and an inflation port 58. The inflation port may be connected to a source of inflation fluid 7 (see FIGS. 7-10).

The delivery tube 14 includes first and second lumens 28, 30, and a balloon 32. An outlet distal surface 24 may be positioned at a distal opening 36 of the first lumen 28 (see FIGS. 1C and 1D). The balloon 32 may be mounted to delivery tube 14 at a location distal of the distal opening 36 and in flow communication with a distal opening 38 of second lumen 30. Typically, a bioadhesive sealant delivered via manifold 12 passes through first lumen 28 to the distal opening 36. An inflation fluid is typically delivered through second lumen 30 to the balloon 32. The inflation fluid may be delivered to the second lumen 30 via the balloon location device 16 and manifold 12.

The delivery tube 14 may also include a delivery tip 34. Delivery tip 34 is shown in more detail in FIGS. 2A-2C. Delivery tip 34 includes a distal wall 40, a side wall 42, a distal opening 44, a plurality of side openings 46, and a stop surface 48. The portion of delivery tube 14 carrying balloon 32 may be inserted through the distal opening 44 until the outlet distal surface 24 abuts against the stop surface 48 (see FIG. 1D). A space is defined between the distal wall 40 and the outlet distal surface 24 to define a first mixing area 49. The first mixing area 49 may be positioned outside of the first lumen 28 while being positioned within the delivery tip 34. The first mixing area 49 may provide a chamber or space within which the bioadhesive sealant mixes further prior to ejection into the tissue puncture through the side openings 46.

Figure 1A:
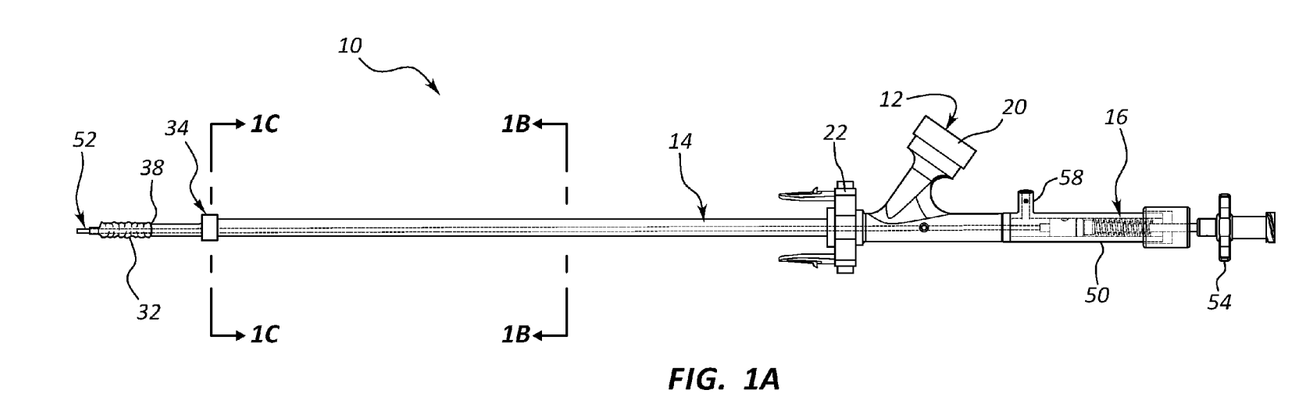
FIG. 1A is a side view of an example vascular closure device in accordance with the present disclosure.
Figure 1B:
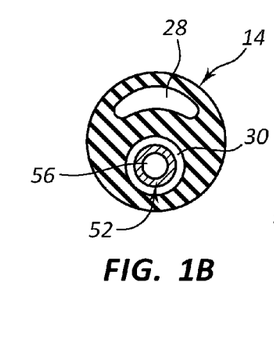
FIG. 1B is a cross-sectional view of the vascular closure device of FIG. 1 taken along cross-section indicators 1B-1B.
Figure 1C:
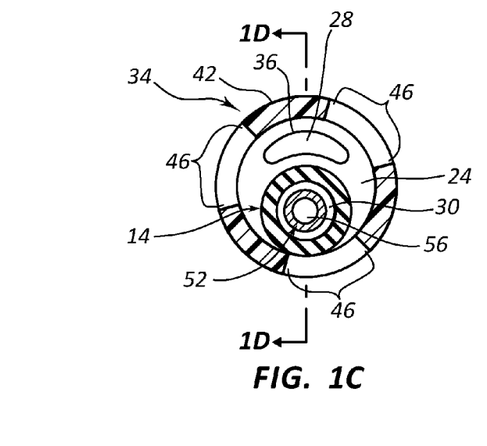
FIG. 1C is a cross-sectional view of the vascular closure device FIG. 1 taken along cross-section indicators 1C-1C.
Figure 1D:
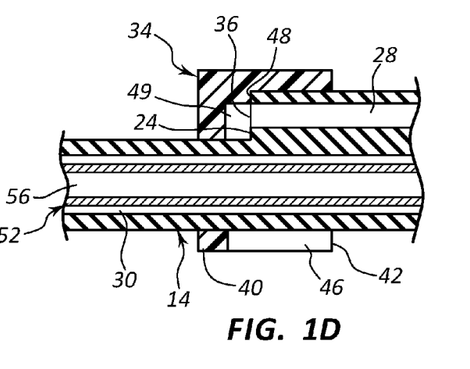
FIG. 1D is a cross-sectional view of the vascular closure device of FIG. 1C taken along cross-section indicators 1D-1D.
Figure 2A:
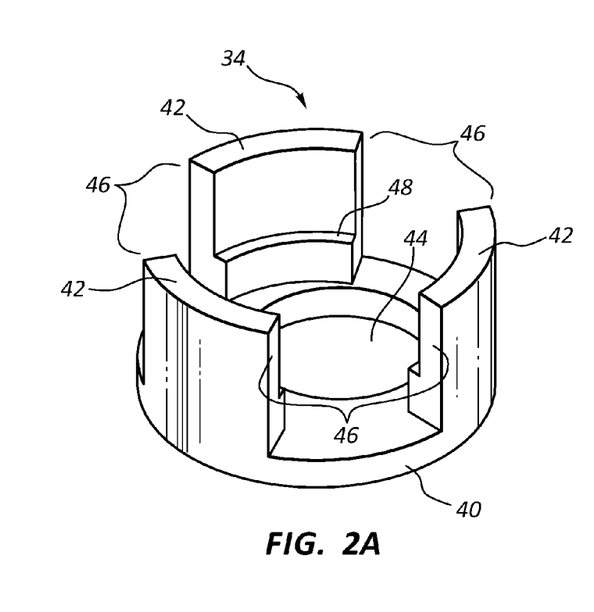
FIG. 2A is a perspective view of a delivery tip of the vascular closure device of FIG. 1.
Figure 2B:
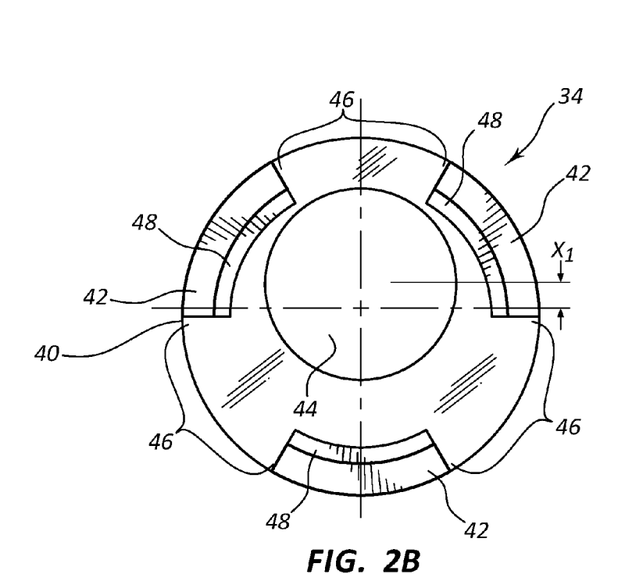
FIG. 2B is a rear view of the delivery tip of FIG. 2A.
Figure 2C:
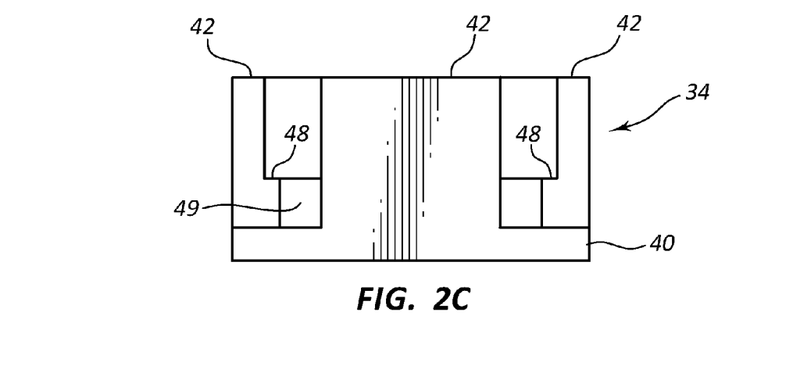
FIG. 2C is a side view of the delivery tip of FIG. 2A.

Delivery tip 34 may provide delivery of the bioadhesive sealant solely in a lateral or radial direction relative to a longitudinal axis of the delivery tube 14. In some arrangements, the distal opening 44 is greater in size than that portion of the delivery tube 14 extending therethrough, thus providing a path for the bioadhesive sealant to exit the delivery tip 34 in an axial or longitudinal direction as well as the lateral direction through the side openings 46. Thus, the delivery tip 34 may provide delivery of the bioadhesive sealant in multiple directions including an axial direction and a lateral or radial direction.

The delivery tip 34 may be permanently attached to delivery tube 14. In some arrangements, the delivery tip 34 may be removeable for purposes of, for example, maintenance or switching with an alternative delivery tip. Delivery tip 34 may be mounted to delivery tube 14 prior to connecting balloon 32 to delivery tube 14.

The distal opening 44 may be offset a distance $X_1$ from a central axis of delivery tip 34 (see FIG. 2B). The offset distance $X_1$ may represent offset of the second lumen 30 from a central axis of delivery tube 14 (see FIG. 1B). In only some arrangements, the distal opening 44 closely matches an outer perimeter size of that portion of delivery tube 14 that extends therethrough to limit flow of the bioadhesive sealant through distal opening 44.

Figure 3A:
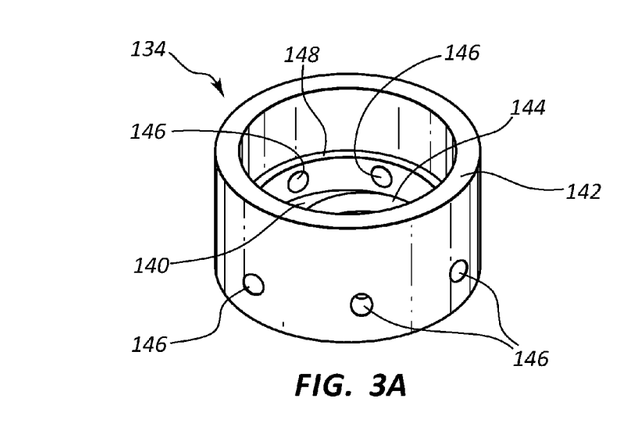
FIG. 3A is a perspective view of another example delivery tip in accordance with the present disclosure.
Figure 3B:
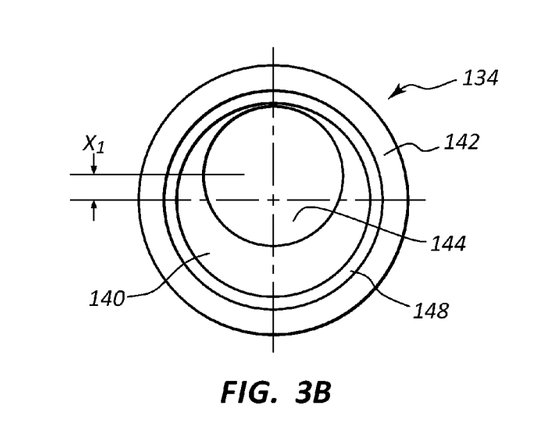
FIG. 3B is a rear view of the delivery tip of FIG. 3A.
Figure 3C:
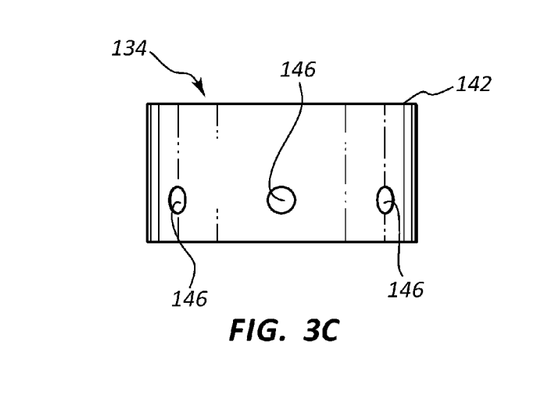
FIG. 3C is a side view of the delivery tip of FIG. 3A.
Figure 3D:
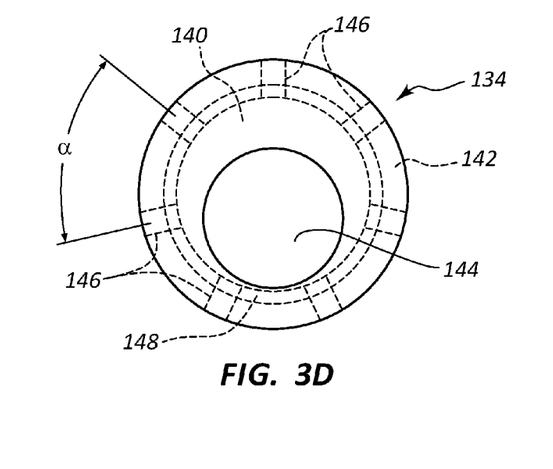
FIG. 3D is a front view of the delivery tip of FIG. 3A.

Referring now to FIGS. 3A-3D, another example delivery tip 134 is shown including a distal wall 140, a side wall 142, a distal opening 144, a plurality of side openings 146, and a stop surface 148. The side wall 142 may be generally continuous around a circumference of side wall 142 without any openings in that portion of the side wall 142 proximal of the stop surface 148. The side openings 146 may be positioned distal of the stop surface 148. The side openings 146 may be spaced apart around a circumference of side wall 142. The side openings 146 may be equally spaced apart an angle α as shown in FIG. 3D. In at least one example, delivery tip 134 includes seven side openings 146 equally spaced apart at an angle α of about 51° (see FIG. 3D).

A space within delivery tip 134 between distal wall 140 and stop surface 148 may define a first mixing area (e.g., similar to first mixing area 49 described above) wherein bioadhesive sealant at least partially mixes prior to exit through side openings 146. The first mixing area may be in flow communication with the distal opening 144 and side openings 146.

Side openings 146 may have various sizes, shapes, and relative spacing between each other to help direct the bioadhesive sealant to particular areas within the tissue puncture. In one example, at least some of these side openings are arranged perpendicular to a longitudinal axis of the delivery tube 14. In other arrangements, at least one of the side openings is arranged at an angle that is neither perpendicular to nor parallel with a longitudinal axis of the delivery tube 14. The side openings 146 may direct the bioadhesive sealant in a direction that is at least partially longitudinal rather than solely laterally or radially.

The distal opening 144 may be offset a distance $X_1$ (see FIG. 3B) from a central axis of delivery tip 134. In at least some arrangements, the side opening 146 is sized to permit at least some bioadhesive sealant to flow therethrough while a portion of the delivery tube 14 extends through distal opening 144. In other arrangements, the distal opening 144 is sized to limit flow of bioadhesive sealant in a distal direction therethrough while delivery tip 134 is mounted to delivery tube 14.

FIGS. 4A-4D illustrate another example vascular closure device 200. Vascular closure device 200 includes a manifold 12, a delivery tube 214, and a balloon location device 16. Delivery tube 214 includes features at a distal end portion thereof that may assist in mixing the bioadhesive sealant and controlling directionality of delivery of the bioadhesive sealant ejected to the tissue puncture. Delivery tube 214 includes first and second lumens 228, 230, and a balloon 232. First lumen 228 has a distal opening 236 at an outlet distal surface 224 (see FIG. 4C). Balloon 232 is mounted at a distal end of delivery tube 214 and in fluid communication with a distal opening 238 of second lumen 230.

Figures 4A, 4B, 4C:
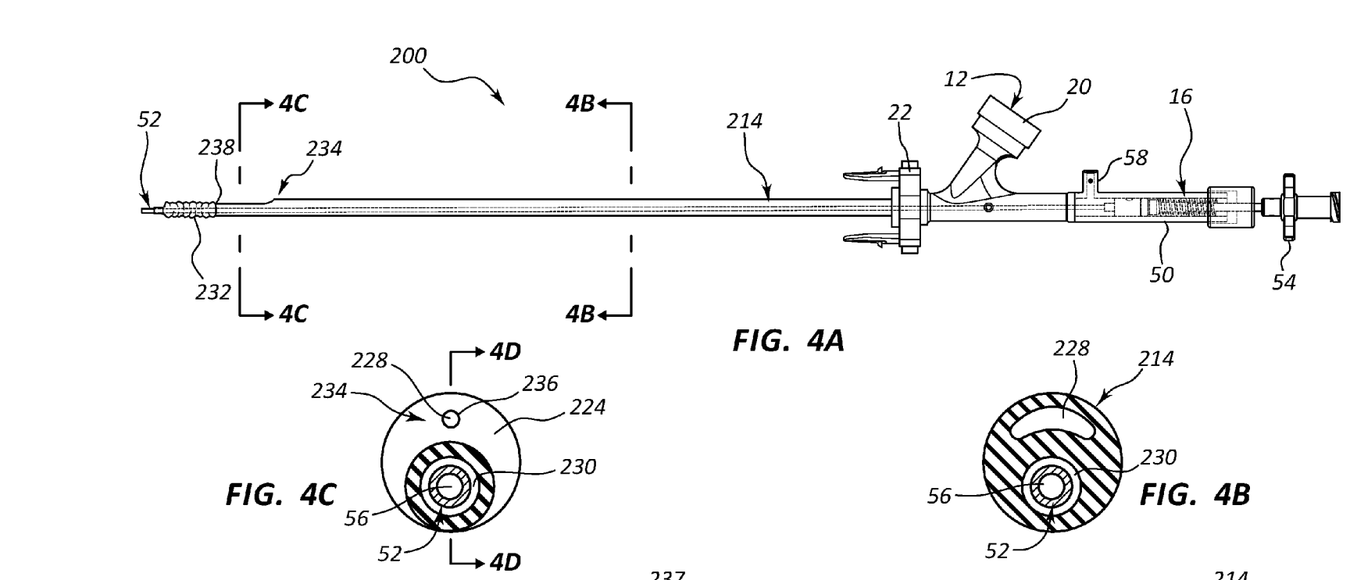
FIG. 4A is a side view of another example vascular closure device in accordance with the present disclosure.
FIG. 4B is a cross-sectional view of the vascular closure device of FIG. 4A taken along cross-section indicators 4B-4B.
FIG. 4C is a cross-sectional view of the vascular closure device of FIG. 4A taken along cross section indicators 4C-4C.
Figure 4D:
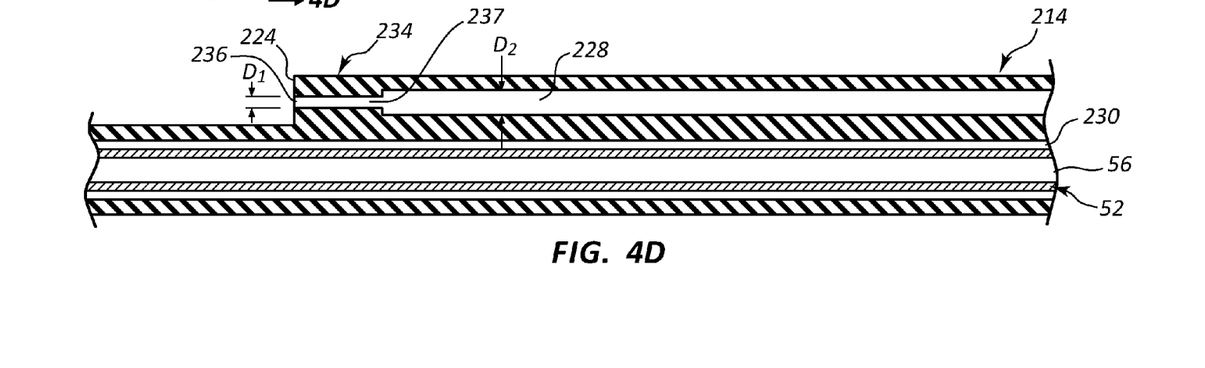
FIG. 4D is a cross-sectional view of the vascular closure device of FIG. 4C taken along cross-section indicators 4D-4D.

Delivery tube 214 includes a delivery tip portion 234 that includes a distal restricted portion 237 in the first lumen 228 (see FIG. 4D). The first lumen 228 may change from a first size having a dimension $D_2$ (see FIG. 4B) to a smaller, restricted size at the distal restricted portion 237 having a dimension $D_1$ (see FIG. 4D). The smaller size of the distal restricted portion 237 functions to accelerate the bioadhesive sealant prior to ejection through distal opening 236. The increased speed in which the bioadhesive exits distal opening 236 may provide a spray effect that creates at some additional dispersion and mixing of the bioadhesive sealant. The change in flow of the bioadhesive sealant as a result of the distal restricted portion 237 may include increased flow turbulence, eddies, and other phenomenon that will help in further mixing of components of the bioadhesive sealant and flow of the bioadhesive sealant within the tissue puncture.

The distal restricted portion 237 may be formed by, for example, heat setting, molding, or thermally reflowing material of the delivery tube 214 at the distal end portion thereof. The delivery tip portion 234 may be integrally formed as a single piece with the rest of delivery tube 214. Alternatively, delivery tip portion 234, including distal restricted portion 237, may be formed separately from the remainder of delivery tube 214 and attached in a separate assembly step. Attachment may include, for example, cold molding, adhesive bonding, and laser welding.

Delivery tip portion 234 may be constructed so that it does not increase the outer profile of delivery tube 214 (e.g., compare FIGS. 4B and 4C). Alternatively, delivery tip portion 234 may provide a reduced size outer profile as compared to other portions of delivery tube 214 proximal of delivery tip portion 234, which may improve ease of insertion of vascular closure device 200 into the tissue puncture.

Referring now to FIGS. 5A-5D, another example vascular closure device 300 includes a manifold 12, a delivery tube 314, and a balloon location device 16. Delivery tube 314 includes first and second lumens 328, 330, and a balloon 332. First lumen 328 includes a plurality of distal openings 336A-E that define at least in part a delivery tip portion 334. Distal openings 336A-E terminate at an outlet distal surface 324. A distal opening 338 of second lumen 330 is typically positioned distal of the distal openings 336A-E and in flow communication with balloon 332.

Delivery tip portion 334 includes a distal restricted portion 337. Distal restricted portion 337 may include a plurality of passages interposed between the first lumen 328 (see FIG. 5B) and the distal openings 336A-E (see FIG. 5D). The passages defined in the distal restricted portion 337 (see FIG. 5C) may have a net cross-sectional area that is less than a cross-sectional area defined by first lumen 328 (see FIG. 5B). A distal restricted portion 337 may accelerate the bioadhesive cement as it passes therethrough and out of the distal openings 336A-E. The distal restricted portion 337 may be formed and function at least in part similar to the distal restricted portion 237 described above. The use of a plurality of distal openings 336A-E in flow communication with a single first lumen 328 may assist in mixing the bioadhesive sealant as it first enters the distal restricted portion 337 and then exits the plurality of distal openings 336A-E to be mixed together within the tissue puncture.

Figure 5A:
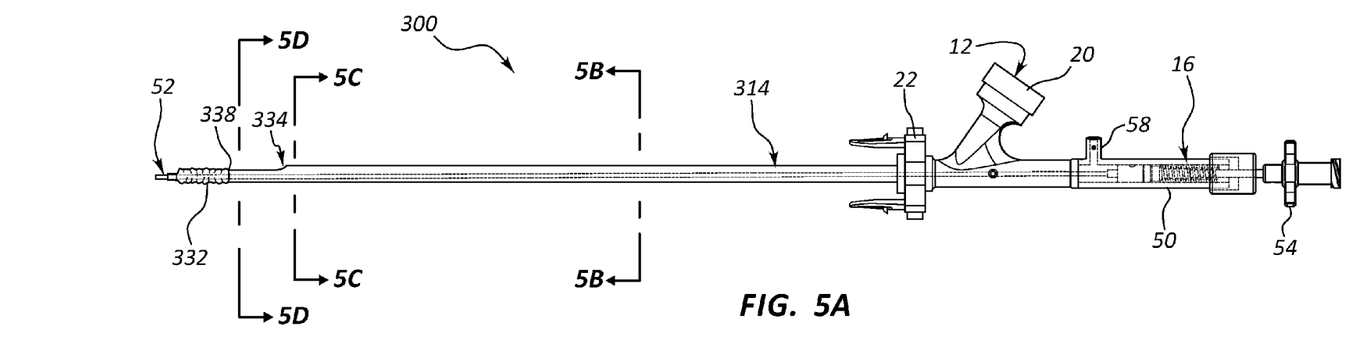
FIG. 5A is a side view of another example vascular closure device in accordance with the present disclosure.
Figure 5B:
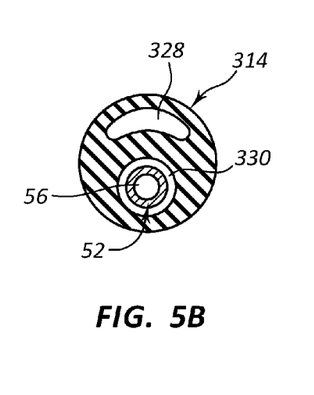
FIG. 5B is a cross-sectional view of the vascular closure device of FIG. 5A taken along cross-section indicators 5B-5B.
Figure 5C:
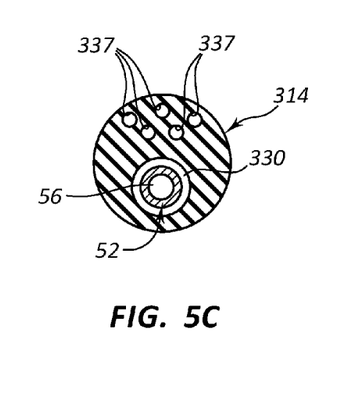
FIG. 5C is a cross-sectional view of the vascular closure device of FIG. 5A taken along cross-section indicators 5C-5C.
Figure 5D:
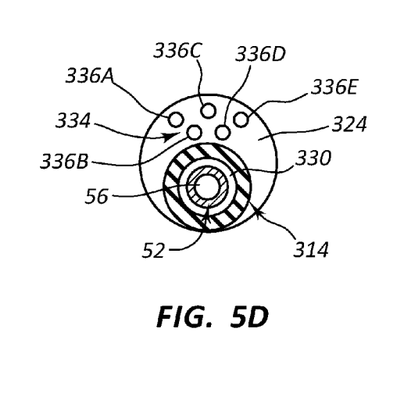
FIG. 5D is a cross-sectional view of the vascular closure device of FIG. 5A taken along cross-section indicators 5D-5D.
Figure 8:
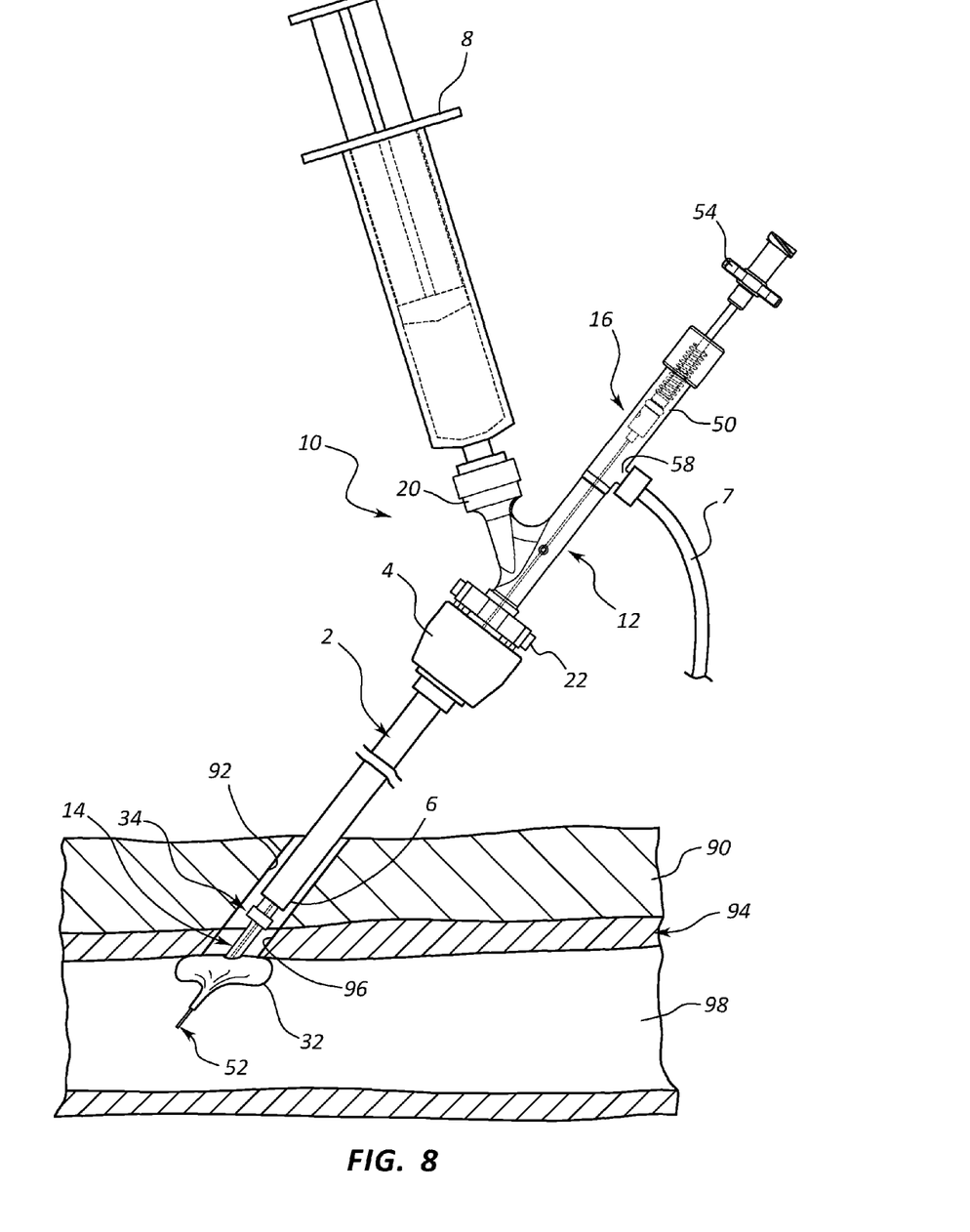

In alternative embodiments, the distal restricted portion 337 is sized and arranged to decelerate the bioadhesive sealant at the distal end of first lumen 328. Such deceleration of the bioadhesive sealant may assist in limiting flow to the bioadhesive sealant through, for example, a vessel puncture and into the vessel beyond a temporary sealing member (e.g., inflated balloon) as seen in FIG. 8. The distal restricted portion 337 may separate the bioadhesive sealant and then recombine the bioadhesive sealant upon ejection through the distal openings 336A-E to provide improved mixing of the bioadhesive sealant and flow within the tissue puncture.

Figure 6A:
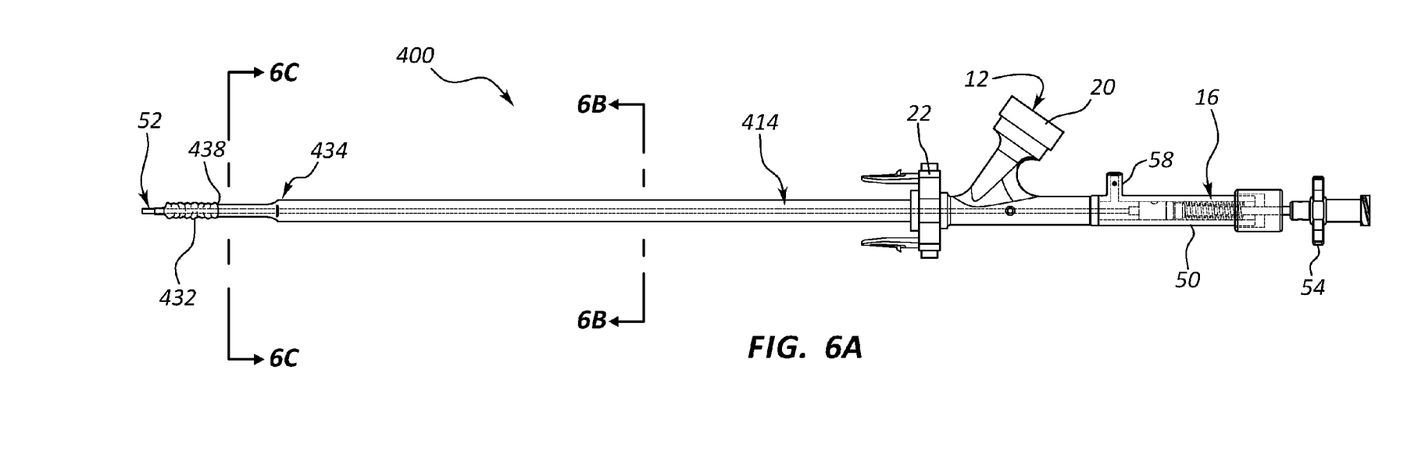
FIG. 6A is a side view of another example vascular closure device in accordance with the present disclosure.
Figure 6B:
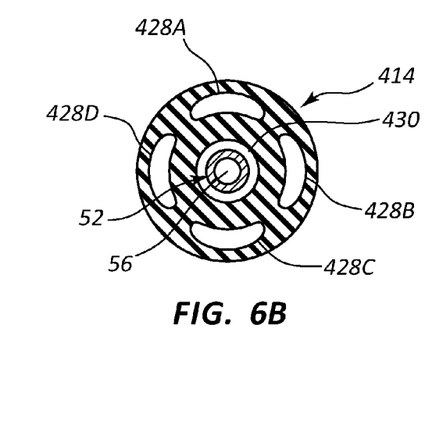
FIG. 6B is a cross-sectional view of the vascular closure device of FIG. 6A taken along cross-section indicators 6B-6B.
Figure 6C:
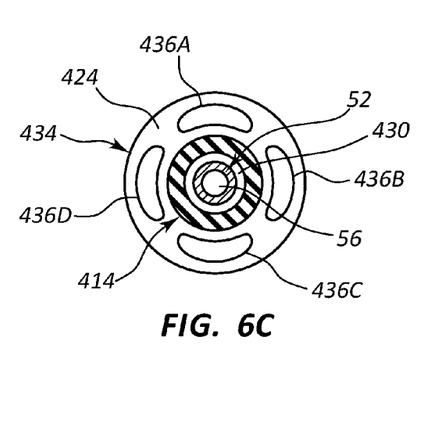
FIG. 6C is a cross-sectional view of the vascular closure device of FIG. 6A taken along cross-section indicators 6C-6C.

FIGS. 6A-6C show another example vascular closure device 400 that includes a manifold 12, a delivery tube 414, and a balloon location device 16. The delivery tube 414 includes a plurality of first lumens 428A-D, which are arranged in flow communication with the injection port 20 of manifold 12. A plurality of distal openings 436A-D may be positioned at an outlet distal surface 424 spaced around a second lumen 430 (see FIG. 6C). The second lumen 430 includes a distal opening 438. The distal openings 436A-D may be aligned and in flow communication with the first lumens 428A-D, respectively. The first lumens 428A-D and distal openings 436A-D may have any desired size, cross-sectional shape, and spacing relative to each other and the second lumen 430. FIGS. 6B and 6C show the first lumens 428A-D and distal openings 436A-D equally spaced apart from each other and from the second lumen 430.

The use of a plurality of distal openings 436A-D may help distribute the bioadhesive sealant more evenly within the tissue puncture and around the delivery tube 414. Equally spacing apart the distal openings 436A-D around the second lumen 430 may also provide more even distribution of the bioadhesive sealant within the tissue puncture. The bioadhesive sealant delivered through the distal openings 436A-D and into the tissue puncture may be further mixed within the tissue puncture as the bioadhesive sealant flows around the delivery tube 414 and within the tissue puncture.

The distal openings of delivery tubes 214, 314, 414 shown with reference to FIGS. 4A-6C are open and facing in a distal direction generally parallel to a longitudinal axis of the delivery tube. Other arrangements are possible in which the openings are arranged non-parallel to the longitudinal axis and at least partially in a radial direction. Furthermore, additional distal openings may be provided extending through a sidewall of the delivery tube in a radial direction and intersecting with the first lumen or distal restricted portion of the delivery tube to provide flow of the bioadhesive sealant in multiple directions (e.g., in an axial and a radial direction) within the tissue puncture.

Figure 7:
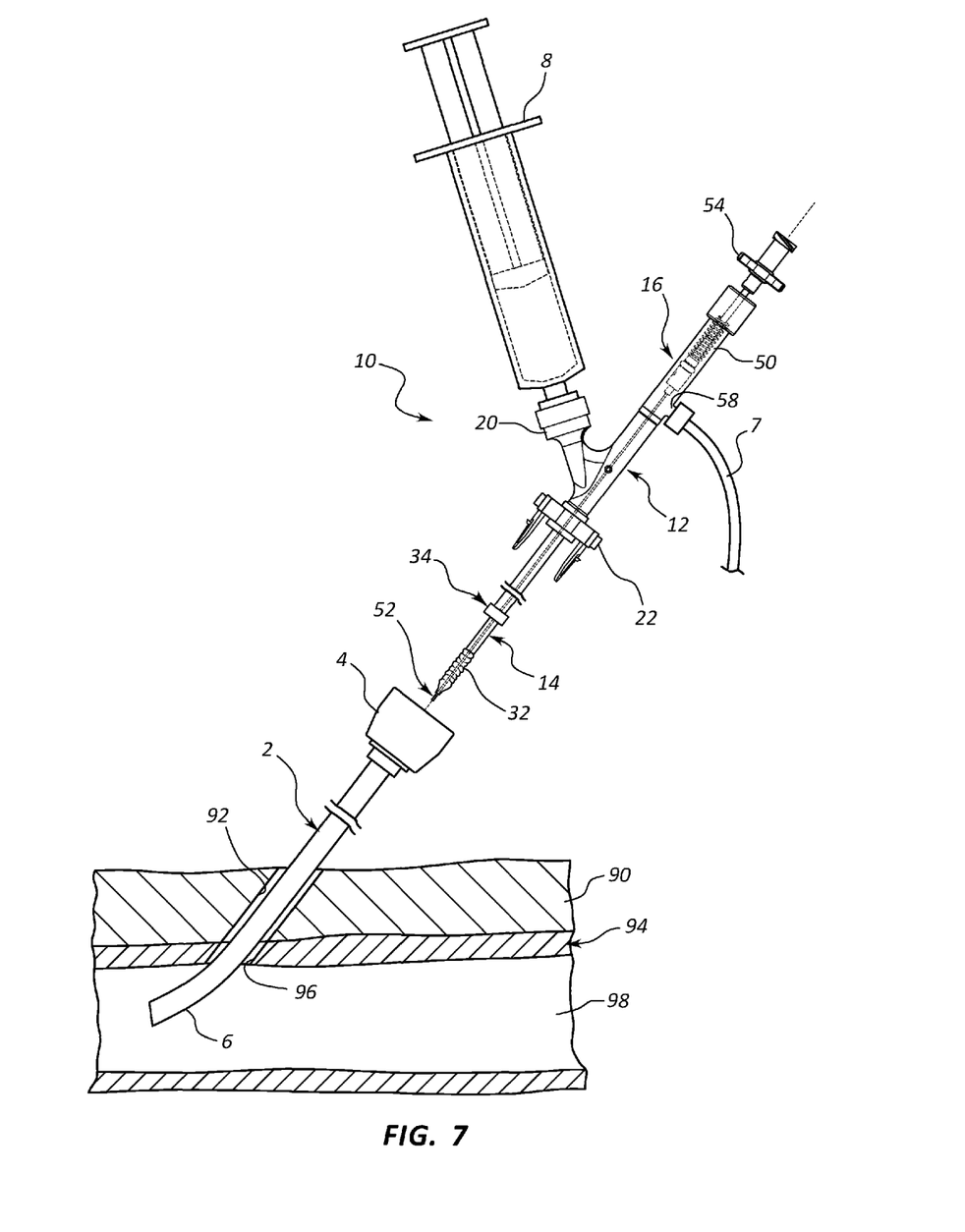
FIGS. 7-10 show use of the vascular closure device of FIG. 1 in a method of sealing a vessel puncture in accordance with the present disclosure.

Referring now to FIGS. 7-10, an example method of sealing a tissue puncture is shown using the vascular closure device 10 of FIGS. 1A-2C. FIG. 7 shows a sheath 2 inserted through a tissue tract 92 of a tissue layer 90 and through a vessel puncture 96 of a vessel 94 so that a distal end 6 of the sheath 2 is positioned within vessel lumen 98. The vascular closure device 10 is aligned with an opening in a hub 4 of sheath 2. FIG. 8 shows the vascular closure device 10 inserted through sheath 2 to position balloon 32 within vessel lumen 98. The latch 22 of manifold 12 may be attached to sheath 2 as shown in FIG. 8 so that the vascular closure device 10 and sheath 2 move in tandem. Balloon 32 is inflated using a volume of inflation fluid provided by the inflation source 7 that is attached to the balloon location device 16. The inflated balloon 32 temporarily seals the vessel puncture 96 from within vessel 94.

A volume of bioadhesive sealant is delivered from a first sealant carrier 8, which is attached to injection port 20 of manifold 12, through first lumen 28 and delivery tip 34 into tissue tract 92 and vessel puncture 96. The bioadhesive sealant may flow from the delivery tip 34 in a radial direction. Once ejected from delivery tip 34, the bioadhesive sealant may flow proximally and distally within tissue tract 92 and vessel puncture 96 to seal the vessel puncture 96 from outside of vessel lumen 98. The bioadhesive sealant may form a sealant plug 5.

Figure 9:
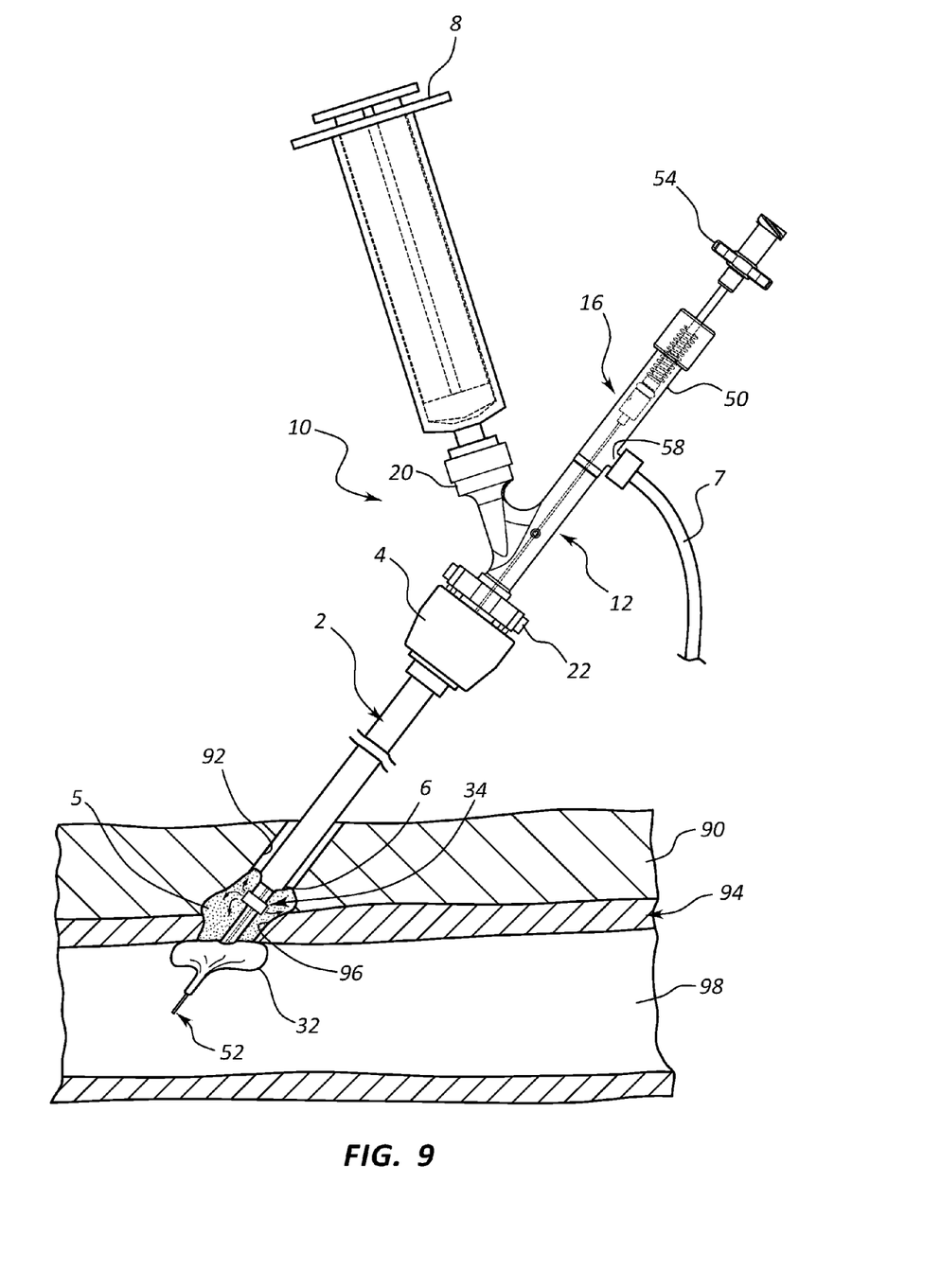
Figure 10:
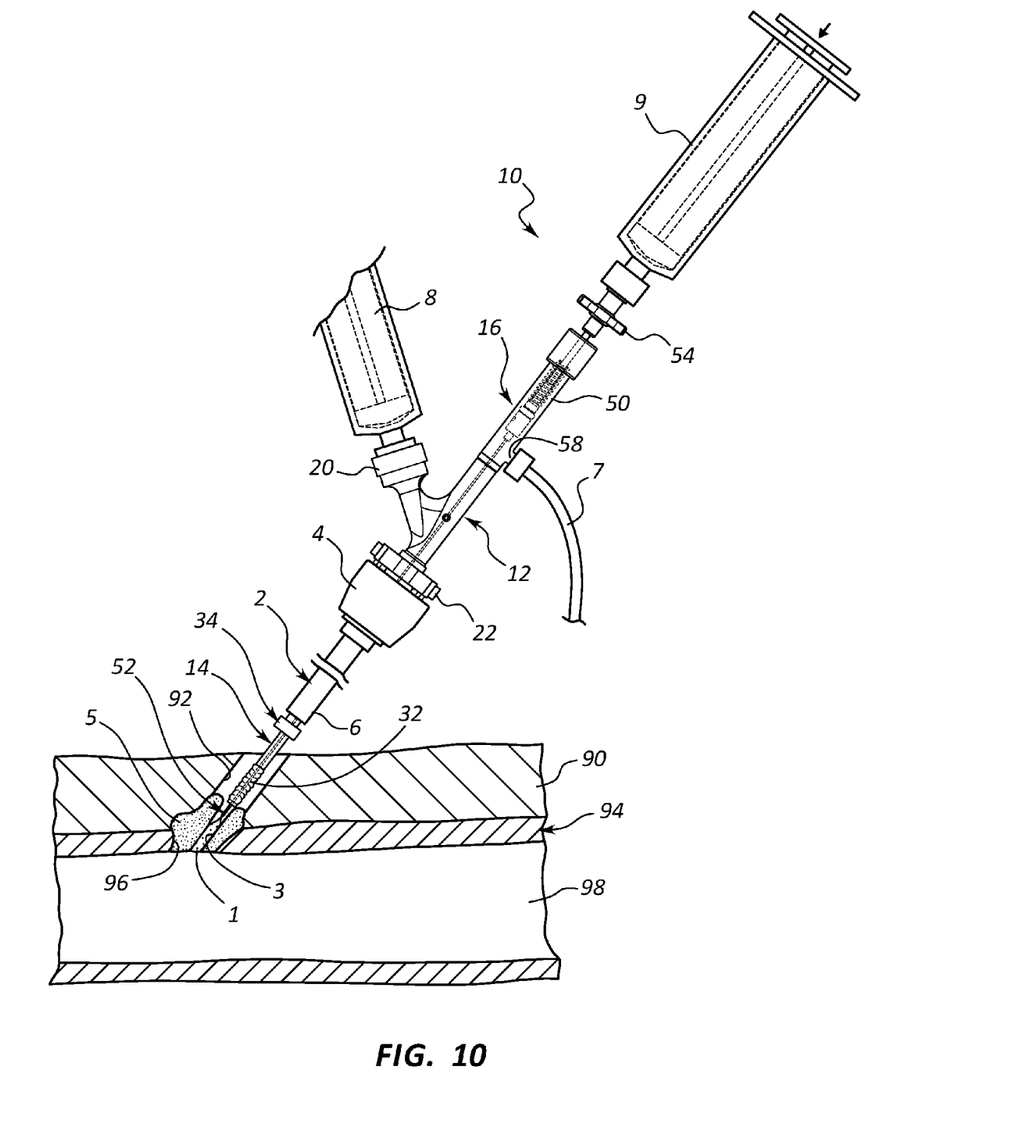

Once the sealant plug 5 is formed (e.g., by curing into a solid or semi-solid state), the balloon 32 is deflated and the vascular closure device 10 withdrawn through the sealant plug 5. Removing the vascular closure device 10 from the sealant plug 5 leaves a plug tract 3 within sealant plug 5. The plug tract 3 may be filled by depositing a secondary sealant plug 1 using a source of secondary sealant carried by a second sealant carrier 9. The secondary sealant may be delivered through the inner tube 52 of balloon location device 16. Alternatively, a secondary sealant may be delivered through the first lumen 28 of delivery tube 14. Alternatively, a detachable tip carried by inner tube 52 at a distal most end of vascular closure device 10 may be detached within the sealant plug 5 to seal the plug tract 3. Further deposits of secondary sealant may be made proximal of sealant plug 5 to further seal tissue tract 92 and vessel puncture 96.

Any one of the delivery tubes and associated delivery tips and delivery tip portions described above with reference to FIGS. 1A-6C may be used to seal a vessel puncture and tissue tract similar to the method shown with respect to FIGS. 7-10.

The sealants discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
    a delivery tube comprising:
       a distal end portion insertable into a tissue puncture;
       a proximal portion positioned proximal of the distal end portion;
       a sealant lumen configured to deliver a sealant to the tissue puncture;
       an inflation lumen;
    a delivery tip having at least a portion being one of a larger size and a larger cross-sectional shape than the distal end portion, the delivery tip having a central axis and an offset distal opening, the offset distal opening being laterally offset from the central axis of the delivery tip, the distal end portion of the delivery tube being positioned through the offset distal opening, the inflation lumen extending through the offset distal opening;
    a balloon positioned at the distal end portion of the delivery tube, the balloon being connected in flow communication with the inflation lumen at a location distal of the delivery tip.

2. The tissue puncture closure device of claim 1, wherein the delivery tip includes at least one outlet opening arranged perpendicular to the sealant lumen.

3. The tissue puncture closure device of claim 1, wherein the delivery tip is detachable from the delivery tube.

4. The tissue puncture closure device of claim 3, wherein the delivery tip includes at least two outlet openings.

5. The tissue puncture closure device of claim 1, wherein the delivery tip is integrally formed as a single piece with the delivery tube.

6. The tissue puncture closure device of claim 1, wherein the delivery tip includes a plurality of outlet openings.

7. The tissue puncture closure device of claim 6, wherein the plurality of outlet openings are arranged facing in a distal direction.

8. The tissue puncture closure device of claim 6, wherein the plurality of outlet openings are arranged facing in a direction perpendicular to the sealant lumen.

9. The tissue puncture closure device of claim 1, wherein the delivery tube includes a plurality of sealant lumens each configured to deliver the sealant to the tissue puncture and arranged in flow communication with the delivery tip.

10. The tissue puncture closure device of claim 1, wherein the delivery tip is movable relative to the sealant and inflation lumens.

11. A vascular closure device, comprising:
    an inflation balloon;
    a delivery tube, comprising:
       an inflation lumen configured to deliver inflation fluid to the inflation balloon;
       a sealant lumen configured to deliver a sealant to a vessel puncture;
    a delivery tip having a plurality of lateral side openings, a distal opening, and at least a portion being one of a larger size and a larger cross-sectional shape than the delivery tube, the distal opening being offset from a central axis of the delivery tip;
    wherein the inflation lumen extends through the distal opening of the delivery tip and the inflation balloon is positioned distal to the delivery tip.

12. The vascular closure device of claim 11, wherein the delivery tip is formed integral with the delivery tube.

13. The vascular closure device of claim 11, wherein at least one of the lateral side openings faces in a direction perpendicular to the sealant lumen.

14. The vascular closure device of claim 11, wherein at least one of the plurality of lateral side openings has a cross-sectional size that is smaller than a cross-sectional size of the sealant lumen.

15. The vascular closure device of claim 11, wherein the delivery tube includes a plurality of sealant lumens each connected in flow communication with the delivery tip.

* * * * *